United States Patent
Yamato et al.

(10) Patent No.: US 9,861,344 B2
(45) Date of Patent: Jan. 9, 2018

(54) OVULATION DAY ESTIMATION APPARATUS, OVULATION DAY ESTIMATION METHOD AND STORAGE MEDIUM IN WHICH OVULATION DAY ESTIMATION PROGRAM IS RECORDED

(71) Applicant: TDK Corporation, Minato-Ku, Tokyo (JP)

(72) Inventors: Kumiko Yamato, Kawasaki Kanagawa (JP); Kazunori Hashimoto, Konosu Saitama (JP)

(73) Assignee: TDK Corporation, Tokyo (JP)

(*) Notice: Subject to any disclaimer, the term of this patent is extended or adjusted under 35 U.S.C. 154(b) by 671 days.

(21) Appl. No.: 14/484,029

(22) Filed: Sep. 11, 2014

(65) Prior Publication Data
US 2015/0250457 A1    Sep. 10, 2015

(30) Foreign Application Priority Data
Mar. 10, 2014    (JP) .................. 2014-046720

(51) Int. Cl.
*A61B 5/00*    (2006.01)
*A61B 10/00*   (2006.01)

(52) U.S. Cl.
CPC .. *A61B 10/0012* (2013.01); *A61B 2010/0019* (2013.01)

(58) Field of Classification Search
CPC .................. A61B 5/01; A61B 10/0012; A61B 2010/0019
USPC ................................ 600/549, 551
See application file for complete search history.

(56) References Cited

U.S. PATENT DOCUMENTS

| 6,110,125 | A  | * | 8/2000  | Young    | A61B 10/0012 600/551 |
| 7,214,196 | B2 | * | 5/2007  | Kodama   | A61B 5/0537 600/551 |
| 8,374,989 | B2 | * | 2/2013  | Lee      | A61B 10/0012 514/171 |
| 8,540,644 | B2 | * | 9/2013  | Husheer  | A61B 5/0008 374/100 |
| 8,632,474 | B2 | * | 1/2014  | Saini    | A61B 10/0012 600/551 |
| 8,821,407 | B2 | * | 9/2014  | Kirsner  | A61B 10/0012 600/551 |
| 8,998,822 | B2 | * | 4/2015  | Rechberg | A61B 5/01 600/551 |
| 9,155,523 | B2 | * | 10/2015 | James    | A61B 10/0012 |
| 9,592,033 | B2 | * | 3/2017  | Toriumi  | A61B 5/746 |

FOREIGN PATENT DOCUMENTS

JP    11-316161 A    11/1999

OTHER PUBLICATIONS

Japanese Office Action dated Sep. 5, 2017 in counterpart Japanese Patent Application No. 2014-048720.

* cited by examiner

*Primary Examiner* — Max Hindenburg
(74) *Attorney, Agent, or Firm* — White & Case LLP

(57) ABSTRACT

According to an embodiment, a server detects temperature increase in basal body temperature measured later relative to basal body temperature measured earlier between chronologically adjacent pieces of basal body temperature data, among basal body temperature data between a menstruation starting day and a next menstruation starting day; and estimates an ovulation day on the basis of the detected temperature increase.

12 Claims, 8 Drawing Sheets

OVULATION DAY ESTIMATION APPARATUS, OVULATION DAY ESTIMATION METHOD AND STORAGE MEDIUM IN WHICH OVULATION DAY ESTIMATION PROGRAM IS RECORDED

CROSS-REFERENCE TO RELATED APPLICATION

This application is based upon and claims the benefit of priority from the Japanese Patent Application No. 2014-46720, filed on Mar. 10, 2014; the entire contents of which are incorporated herein by reference.

FIELD

An embodiment described herein relates generally to an ovulation day estimation apparatus for estimating a woman's ovulation day, an ovulation day estimation method and a storage medium in which ovulation day estimation program is recorded.

BACKGROUND

Recently, various kinds of healthcare support systems for women useful for promotion of pregnancy and contraception, basal body temperature measurement systems using a mobile information terminal such as a mobile phone, menstrual cycle estimation programs used for a woman to estimate her menstrual cycle, and the like have been proposed. Such systems will be helpful for a user in promotion of pregnancy, health care management and the like by providing various kinds of information to the user on the basis of data of a menstrual cycle.

Information that can be used as a basis for promotion of pregnancy for women includes menstrual days and an ovulation day. Women's menstrual days and ovulation day are thought to have a regular periodicity.

Among the systems proposed so far, however, though there are systems which can estimate whether ovulation occurs or not, there are not systems which can estimate an ovulation day. Actually, a woman cannot know her own ovulation day unless she undergoes an examination.

If an ovulation day can be estimated, accuracy of predicting a next ovulation day can be improved. Furthermore, if an ovulation day can be estimated, it is possible to accurately separate a low temperature period and a high temperature period, and, therefore, it is possible to improve accuracy of determining a hormone balance state from change in basal body temperature.

DETAILED DESCRIPTION

An ovulation day estimation apparatus of an embodiment has a temperature increase detection section configured to detect temperature increase in basal body temperature measured later relative to basal body temperature measured earlier between chronologically adjacent pieces of basal body temperature data, among basal body temperature data between a menstruation starting day and a next menstruation starting day; and an estimation section configured to estimate an ovulation day on the basis of the detected temperature increase.

An embodiment will be described below with reference to drawings.

Configuration

Figure 1:
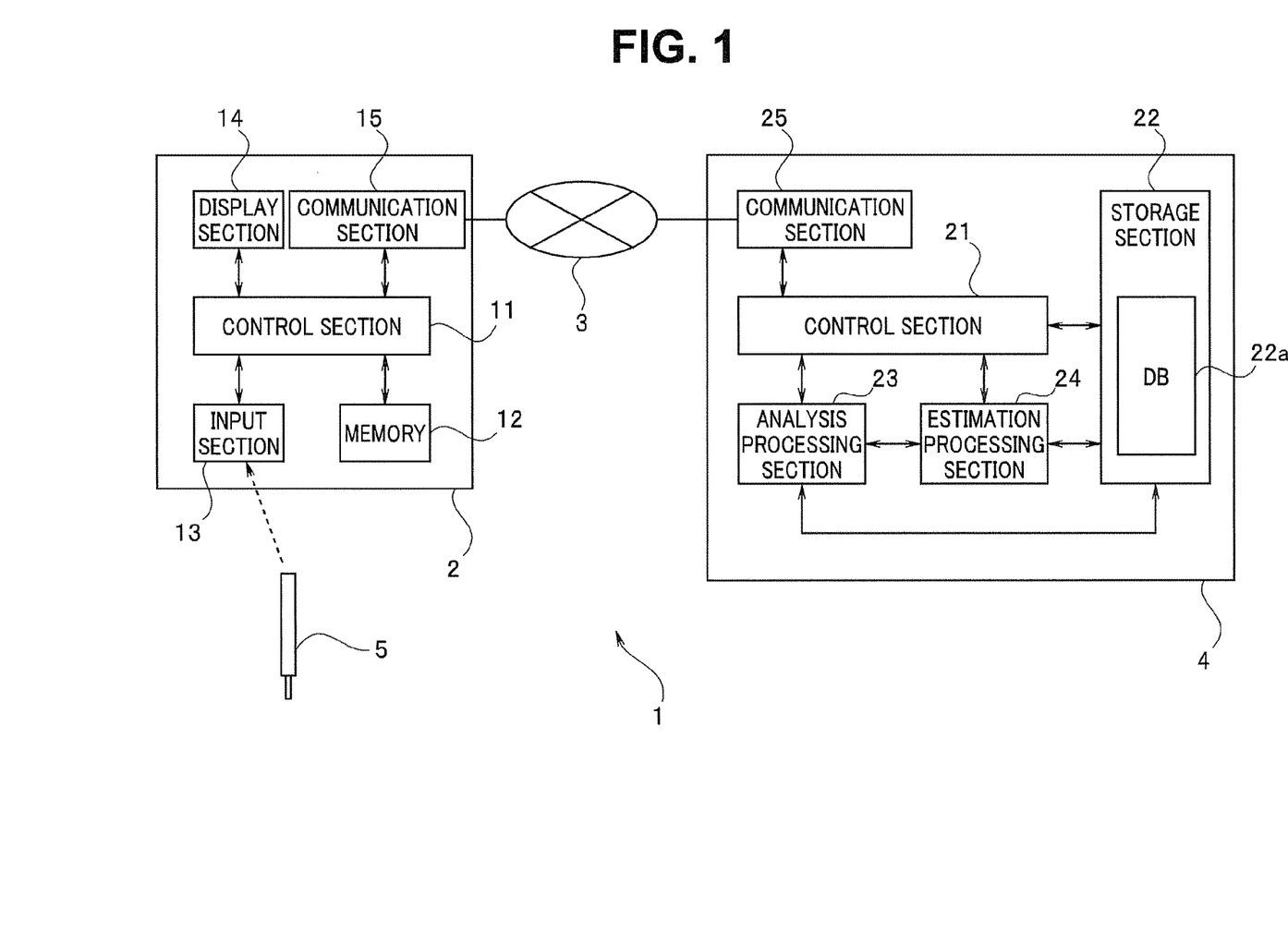
FIG. 1 is a block diagram of an ovulation day estimation system according to an embodiment.

FIG. 1 is a block diagram of an ovulation day estimation system according to an embodiment.

An ovulation day estimation system 1 includes a smartphone 2 and a server 4 connected to the smartphone 2 via a network 3. Data of basal body temperature measured by a thermometer 5 is inputted to the smartphone 2. In FIG. 1, only one smartphone 2 is shown in FIG. 1. In the ovulation day estimation system 1, however, multiple smartphones 2 are communicably connected to the server 4 via the network 3, and the server 4 collects and stores basal body temperature data and the like of a lot of users having the smartphones 2. That is, the server 4 has data about women's menstrual cycle and basal body temperature, and it is an ovulation day estimation apparatus which estimates users' ovulation day as described later.

The smartphone 2, which is a mobile terminal, includes a control section 11, a memory 12, an input section 13, a display section 14 and a communication section 15. The control section 11 has a central processing unit (CPU), a ROM, a RAM and the like, and it is a processing section which executes a program stored in the ROM or the like or the program downloaded via the network 3 to execute a predetermined function.

Note that, though the smartphone 2 communicates with the server 4 here, a tablet terminal, a personal computer, a dedicated terminal or the like is also possible instead of the smartphone 2.

The network 3 is a LAN or the Internet.

The memory 12 is a rewritable nonvolatile memory such as a flash memory. In the memory 12, basal body temperature data and the like of a woman, who is a user, and an application program for transmitting the basal body temperature data and the like to the server 4 are stored.

The input section 13 is a touch panel for the user to input basal body temperature data and a menstruation starting day, and it is attached to the display section 14. The display section 14 is a display device like a liquid crystal display.

The communication section 15 has a wireless communication function, and it is a circuit for communicating with a near base station or the like to perform telephone conversation and data communication via the network 3. Thus, the communication section 15 performs data communication with the server 4 under the control of the control section 11.

Note that, in the case of using a personal computer as a terminal for transmitting basal body temperature data and the like instead of the smartphone 2, the communication section 15 may be such that has a wired communication function.

The control section 11 executes a process for reading out and executing the application program stored in the memory 12, storing basal body temperature data and the like inputted from the input section 13 into the memory 12 and transmitting the basal body temperature data and the like to the server 4 via the network 3, and a process for receiving data from the server 4.

Thus, with the use of the application program the user can input data of basal body temperature measured by the thermometer 5 and a menstruation starting day by the input section 13, which is a touch panel, and transmitting them to the server 4.

Note that, though the user manually inputs basal body temperature data here, the input section 13 is a reception circuit for receiving basal body temperature data transmitted from the thermometer 5 if the thermometer 5 has a data transmission function.

The server 4 includes a control section 21, a storage section 22, an analysis processing section 23, an estimation processing section 24 and a communication section 25.

The control section 21 has hardware devices such as a central processing unit (CPU), a ROM and a RAM, and it is a processing section in which the central processing unit (CPU) executes a program stored in a storage device such as the ROM to perform a predetermined function.

The storage section 22 has a database (DB) 22a constituted by data received from the users via the network 3 and various kinds of data obtained by analyzing the data.

The analysis processing section 23 analyzes the user's basal body temperature data and the like transmitted from the smartphone 2 to obtain various kinds of data for estimation of an ovulation day, under the control of the control section 21. The estimation processing section 24 estimates the ovulation day on the basis of the user's basal body temperature data and the various kinds of data obtained by the analysis by the analysis processing section 23, under the control of the control section 21. Though the analysis processing section 23 and the estimation processing section 24 are realized by a software program, they may be realized by hardware circuits. The software program of the analysis processing section 23 and the estimation processing section 24 is stored in the storage section 22.

The communication section 25 performs data communication via the network 3. The communication section 25 performs communication with each smartphone 2 under the control of the control section 21. Thus, the communication section 25 constitutes a basal body temperature information collection section which collects pieces of basal body temperature data of multiple days from the user.

Here, description will be made on change in basal body temperature.

Figure 2:
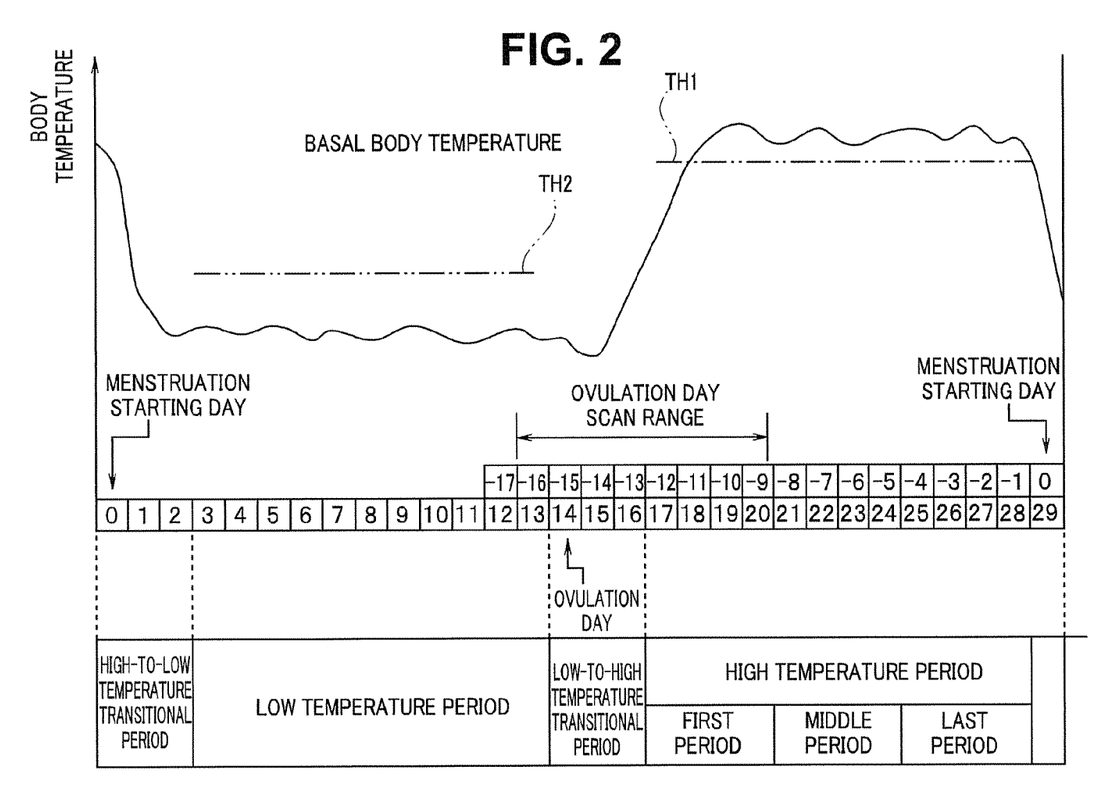
FIG. 2 is a diagram for illustrating change in a woman's basal body temperature from a menstruation starting day to a next menstruation starting day according to the embodiment.

FIG. 2 is a diagram for illustrating change in a woman's basal body temperature from a menstruation starting day to a next menstruation starting day.

FIG. 2 shows an example of change in a woman's basal body temperature from a menstruation starting day to a next menstruation starting day with the menstruation starting day as a 0th day and the next menstruation starting day as a 29th day. In general, the basal body temperature is measured in the mouth (under the tongue) in a state of lying down immediately after getting up in the morning after having a sufficient sleep.

A menstrual cycle has a "high-to-low temperature transitional period" immediately after a menstruation starting day, a "low temperature period", a "low-to-high temperature transitional period" between the low temperature period and a high temperature period, and the "high temperature period" after the low-to-high temperature transitional period. The high temperature period is further divided into a first period, a middle period and a last period.

The menstrual cycle is a period from the menstruation starting day to a day immediately before the next menstruation starting day.

As described above, the user can transmit basal body temperature measured with the thermometer 5 and a menstruation starting day from the smartphone 2 to the server 4 using the application program stored in the memory 12 of the smartphone 2. The server 4 receives data of the basal body temperature and the data of the menstruation starting day from the user and registers them with the database 22a. When at least two menstruation starting days are registered with the database 22a by the user, the server 4 executes a process shown in FIGS. 3 and 4.

Figure 3:
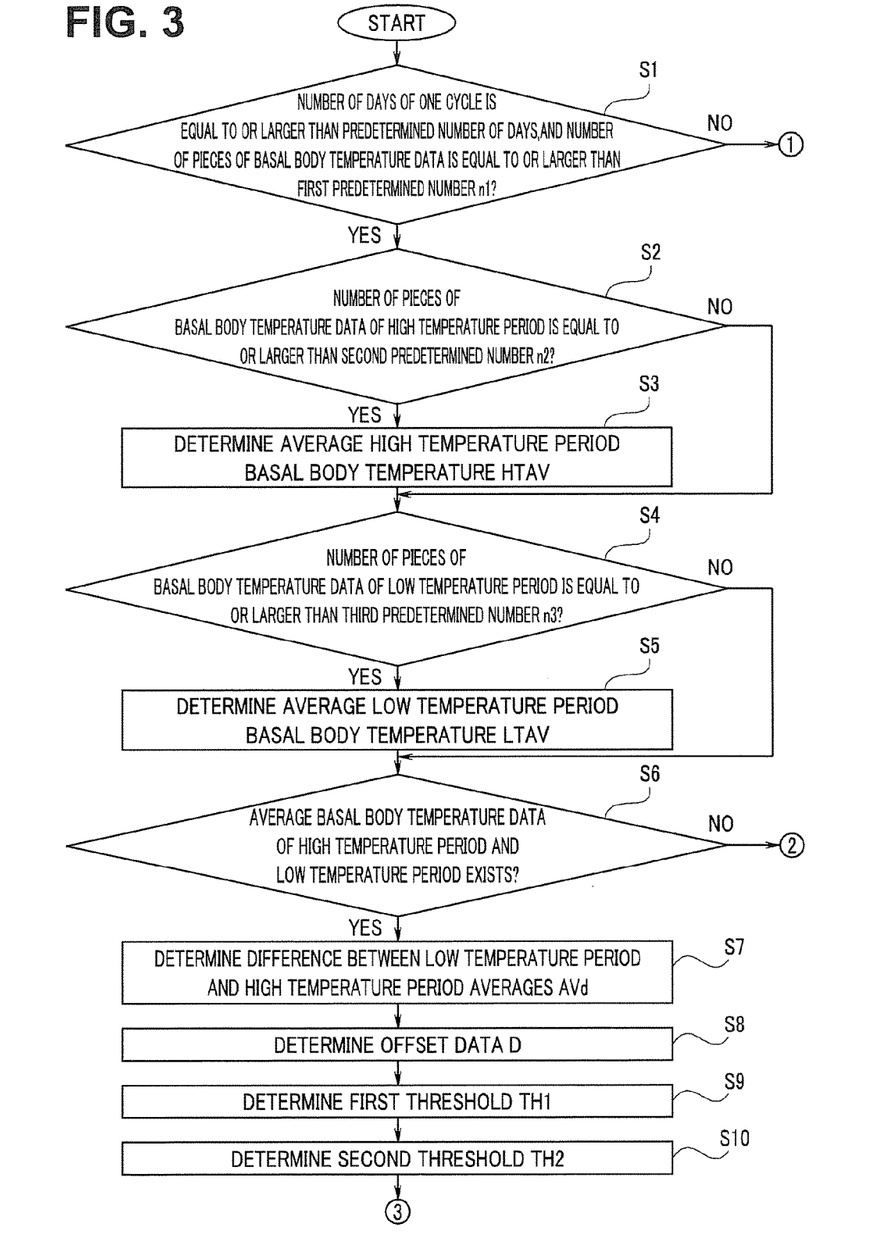
FIG. 3 is a flowchart showing an example of a flow of a process for analyzing basal body temperature data according to the embodiment.
Figure 4:
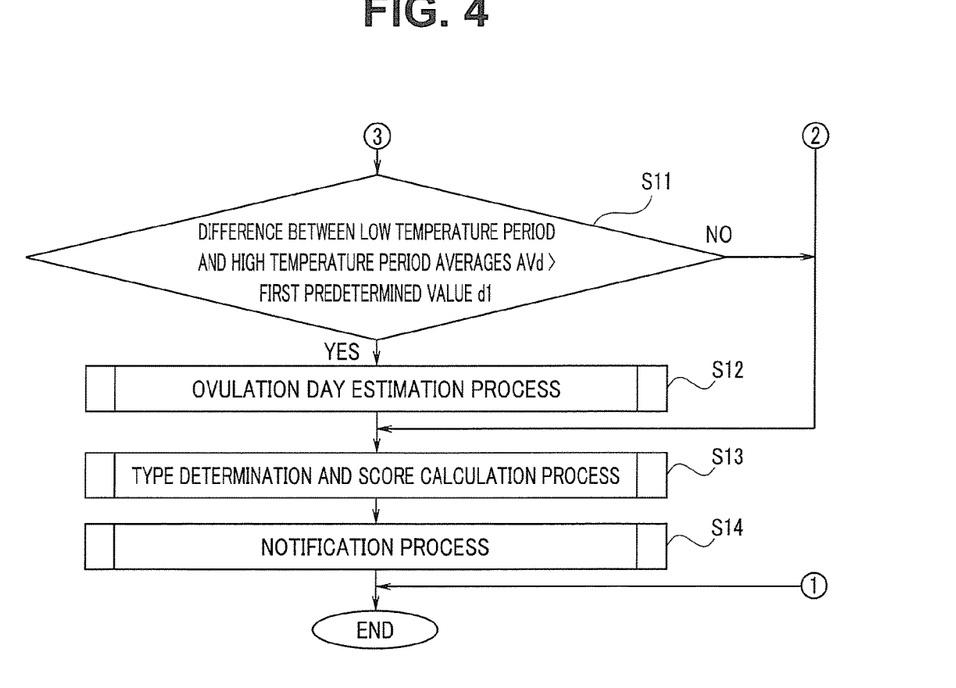
FIG. 4 is a flowchart showing the example of the flow of the process for analyzing basal body temperature data according to the embodiment.

FIGS. 3 and 4 comprise a flowchart showing an example of a flow of a process for analyzing basal body temperature data. The analysis processing section 23 reads out the user's basal body temperature data with which menstruation starting days are registered, from the database 22a and executes the process in FIG. 3 under the control of the control section 21.

Note that, by the analysis process and estimation process described below being executed, estimation of an ovulation day not only becomes possible in the case where basal body temperature data exists for all days within a menstrual cycle but also becomes possible even in the case where the basal body temperature data does not exist for all the days within the menstrual cycle under predetermined conditions.

First, the analysis processing section 23 judges whether or not the number of days of one menstrual cycle is equal to or larger than a predetermined number of days, and the number of pieces of basal body temperature data is equal to or larger than a first predetermined number n1 (S1). The predetermined number of days is, for example, twenty days. The first predetermined number n1 is a number determined in advance, and it is, for example, six here. In the case of a user with the number of days of the menstrual cycle smaller than the predetermined number of days (S1: NO), it is not possible to perform the analysis described below, and the process ends.

Furthermore, in the case where the number of pieces of basal body temperature data is smaller than the first predetermined number n1 determined in advance (S1: NO), it is also not possible to perform the analysis described below, and the process ends.

If the number of days of one menstrual cycle is larger than the predetermined number of days, and the number of pieces of basal body temperature data is equal or larger than the predetermined number n1 (S1: YES), the analysis processing section 23 judges whether or not the number of pieces of basal body temperature data of the high temperature period is equal to or larger than a second predetermined number n2 (S2). The second predetermined number n2 is a number determined in advance, and, it is, for example, eight here. If the number of pieces of basal body temperature data of the high temperature period is less than the second predetermined number n2 (S2: NO), the process transitions to S4.

More specifically, a period from a day twelve days before a menstruation starting day (a 17th day in FIG. 2) to a day before the menstruation starting day (a 28th day in FIG. 2) is assumed to be a provisional high temperature period, and it is judged whether or not the number of pieces of basal body temperature data during the provisional high temperature period is equal to or larger than the second predetermined number n2.

If the number of pieces of basal body temperature data of the high temperature period is equal to or larger than the second predetermined number n2 (S2: YES), the analysis processing section 23 determines average high temperature period basal body temperature HTAV, which is an average of basal body temperatures of the high temperature period (S3).

If the number of pieces of basal body temperature data of the high temperature period is less than the second predetermined number n2 (S2: NO), or after the average high temperature period basal body temperature HTAV is determined, the analysis processing section 23 judges whether or not the number of pieces of basal body temperature data of the low temperature period is equal to or larger than a third predetermined number n3 (S4). The third predetermined number n3 determined in advance is, for example, two here. If the number of pieces of basal body temperature data of the low temperature period is less than the third predetermined number n3 (S4: NO), the process transitions to S6.

More specifically, a period from a third day to 13th day from the menstruation starting day is assumed to be a provisional low temperature period, and it is judged whether or not the number of pieces of basal body temperature data during the provisional low temperature period is equal to or larger than the third predetermined number n3.

If the number of pieces of basal body temperature data of the low temperature period is equal to or larger than the third predetermined number n3 (S4: YES), the analysis processing section 23 determines average low temperature period basal body temperature LTAV, which is an average of basal body temperatures of the low temperature period (S5).

If the number of pieces of basal body temperature data of the low temperature period is less than the third predetermined number n3 (S4: NO), or after the average low temperature period basal body temperature LTAV is determined, the analysis processing section 23 judges whether or not both of the average high temperature period basal body temperature HTAV and the average low temperature period basal body temperature LTAV exist (S6).

If both of the average high temperature period basal body temperature HTAV and the average low temperature period basal body temperature LTAV exist (S6: YES), the analysis processing section 23 determines difference between the average low temperature period basal body temperature LTAV and the average high temperature period basal body temperature HTAV (hereinafter referred to as a difference between low temperature period and high temperature period averages) AVd (S7). The difference between low temperature period and high temperature period averages AVd is a value obtained by subtracting the average low temperature period basal body temperature LTAV from the average high temperature period basal body temperature HTAV. If both of the average high temperature period basal body temperature HTAV and the average low temperature period basal body temperature LTAV do not exist (S6: NO), the process transitions to S13.

After determining the difference between low temperature period and high temperature period averages AVd, the analysis processing section 23 determines offset data D (S8). The offset data D is determined by multiplying the difference between low temperature period and high temperature period averages AVd by a predetermined coefficient. A value obtained by multiplying the difference between low temperature period and high temperature period averages AVd by a first coefficient $\alpha 1$ (that is, AVd*$\alpha 1$) or, for example, 0.15, whichever is larger, is determined as the offset data D here. The first coefficient $\alpha 1$ is, for example, 0.3.

After determining the offset data D, the analysis processing section 23 determines a first threshold TH1 (S9). The first threshold TH1 is a value obtained by subtracting the offset data D from the average high temperature period basal body temperature HTAV (that is, TH1=HTAV-D) here, and it is base body temperature for high temperature period judgment.

After determining the first threshold TH1, which is the base body temperature for high temperature period judgment, the analysis processing section 23 determines a second threshold TH2 (S10). The second threshold TH2 is a value obtained by adding a value obtained by multiplying the difference between low temperature period and high temperature period averages AVd by a second coefficient $\alpha 2$ to the average low temperature period basal body temperature LTAV (that is, TH2=LTAV+$\alpha 2$*AVd) here, and it is base body temperature for low temperature period judgment. The second coefficient $\alpha 2$ is, for example, 0.4.

After determining the second threshold TH2, which is the base body temperature for low temperature period judgment, the analysis processing section 23 judges whether or not the difference between low temperature period and high temperature period averages AVd exceeds a first predetermined value d1 (S11). The first predetermined value d1 is, for example, 0.2° C.

In the case of YES at S11, an ovulation day estimation process (S12) is executed. In the case of NO at S11, the process transitions to S13.

Figure 5:
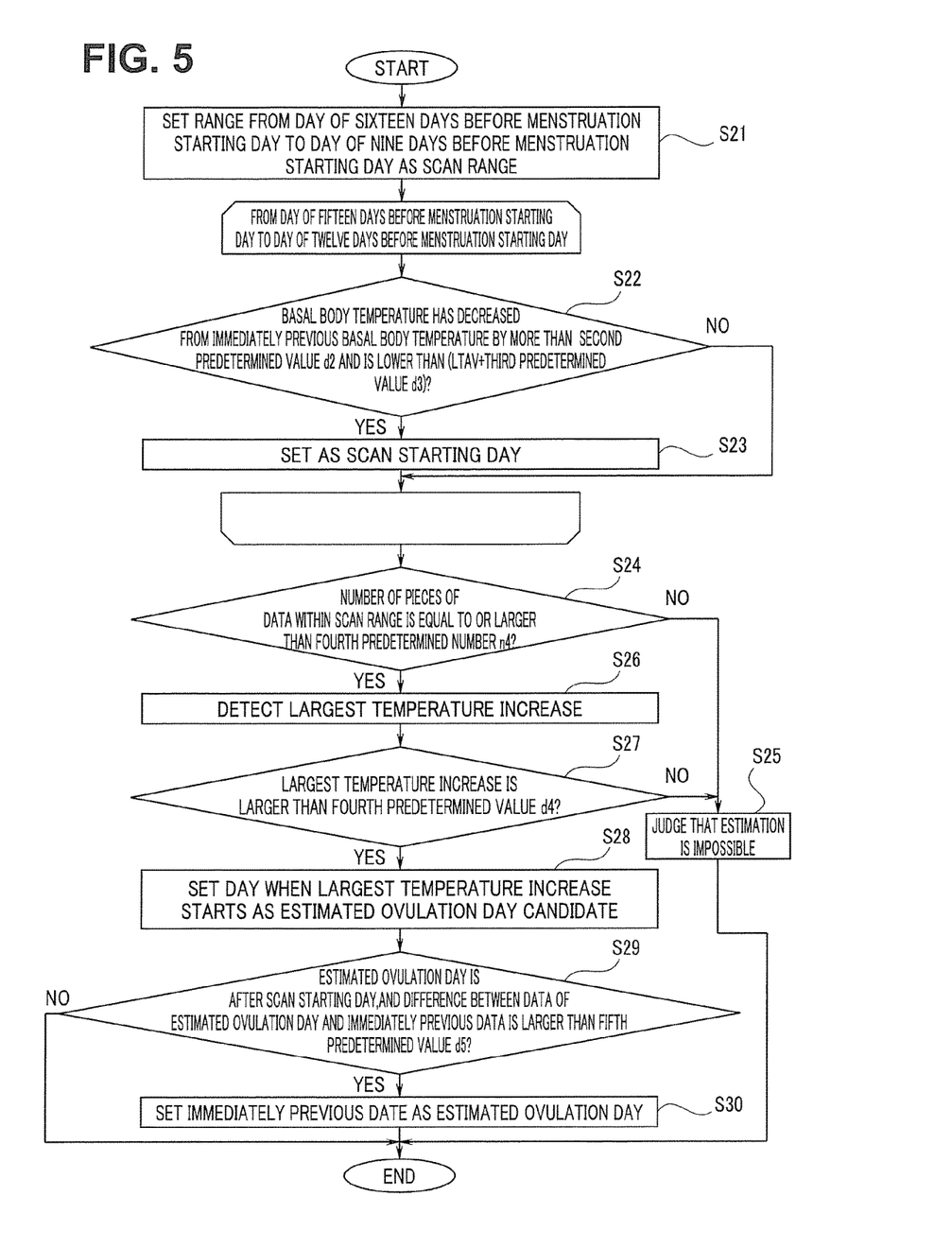
FIG. 5 is a flowchart showing an example of a flow of an ovulation day estimation process (S12) according to the embodiment.

FIG. 5 is a flowchart showing an example of the flow of the ovulation day estimation process (S12). The ovulation day estimation process is executed by the estimation processing section 24.

First, the estimation processing section 24 sets a range from a day sixteen days before the menstruation starting day to a day nine days before the menstruation starting day as a provisional scan range (S21). In the case of FIG. 2, the 13th day is the day sixteen days before the menstruation starting day, and the day is set as a provisional scan starting day first. The provisional scan range corresponds to multiple days set in advance with the menstruation starting day as a reference day (the day sixteen days before the menstruation starting day to the day nine days before the menstruation starting day here), and the earliest day within the provisional scan range (the day sixteen days before the menstruation starting day here) is set as the provisional scan starting day first.

That is, the period from the 13th day (sixteen days before the menstruation starting day) in FIG. 2 to a 20th day (nine days before the menstruation starting day) in FIG. 2 is set as the provisional scan range. The 20th day in FIG. 2 is the day nine days before the menstruation starting day and is a scan ending day.

After the provisional scan range is set as described above, a scan starting day is decided.

Then, the estimation processing section 24 acquires basal body temperature data in order sequentially from the earliest day to the latest day within a range from a day fifteen days before the menstruation starting day (a 14th day in FIG. 2) to the day twelve days before the menstruation starting day (the 17th day in FIG. 2) within the provisional scan range and judges whether or not the acquired basal body temperature data satisfies a predetermined condition (S22). That is, the process of S22 is executed for each piece of basal body temperature data within the provisional scan range. At S22, it is judged, for each piece of basal body temperature data within the provisional scan range, whether or not basal body temperature of a day concerned (basal body temperature measured later between chronologically adjacent pieces of basal body temperature data) decreases from basal body temperature immediately before the day concerned (basal body temperature measured earlier between the chronologically adjacent pieces of basal body temperature data) by more than a second predetermined value d2 and is lower than a value obtained by adding a third predetermined value d3 to the average low temperature period basal body temperature LTAV.

More specifically, the judgment of S22 is performed for basal body temperature data of the day fifteen days before the menstruation starting day (the 14th day in FIG. 2) first. It is judged whether basal body temperature of the day fifteen days before the menstruation starting day decreases from basal body temperature of an immediately previous day (the day sixteen days before the menstruation starting day) by more than the second predetermined value d2 and is lower than the value obtained by adding the third predetermined value d3 to the average low temperature period basal body temperature LTAV (S22). The second predetermined value d2 is, for example, 0.1° C., and the third predetermined value d3 is, for example, 0.1° C.

The judgment process of S22 is executed for all the basal body temperature data of each of days from the day fifteen days before the menstruation starting day to the day twelve days before the menstruation starting day, in order sequentially from the earliest day to the latest day. At the end, the judgment of S22 is performed for the basal body temperature data of the day twelve days before the menstruation starting day (the 17th day in FIG. 2). If the basal body temperature data of a day concerned satisfies the predetermined condition (S22: YES), the day is caused to be the scan starting day (S23).

The process of S22 is executed for all the pieces of basal body temperature data of the days from the day fifteen days before the menstruation starting day to the day twelve days before the menstruation starting day. If the basal body temperature data satisfies the predetermine condition (S22), the scan starting day is updated (S23). If the basal body temperature data does not satisfy the predetermine condition (S22), the scan starting day is not updated. The scan starting day is initially set to the day sixteen days before the menstruation starting day. After that, when basal body temperature data satisfying the predetermined condition exists, the scan starting day is updated. Therefore, if a result of the judgment process of S22 is NO for all the days within the provisional scan range, the scan starting day is the day sixteen days before the menstruation starting day (the 13th day in FIG. 2).

As described above, the process of S21 to S23 constitutes a scan starting day decision section which decides a day on which basal body temperature satisfies a predetermined condition, in order sequentially from the earliest day to the latest day, among pieces of basal body temperature data of multiple successive days set in advance with a menstruation starting day as a base, as a scan range. The judgment about whether basal body temperature data satisfies the predetermined condition or not is performed in order sequentially from the earliest day to the latest day. If there are multiple pieces of basal body temperature data satisfying the predetermined condition, the scan starting day is updated, and the latest day among multiple days becomes the scan starting day. That is, the process of S21 to S23, which is the scan starting day decision section, checks whether or not there is a day when basal body temperature decreases from basal body temperature of an immediately previous day by more than the second predetermined value d2, in order from the earliest day in the scan range, and decides a latest day among days on which basal body temperature decreases by more than the second predetermined value d2 and is lower than the value obtained by adding the third predetermined value d3 to the average low temperature period basal body temperature LTAV (LTAV+d3), as the scan starting day.

Next, the estimation processing section 24 judges whether or not the number of pieces of basal body temperature data within the scan range (a range from the scan starting day to the day nine days before the menstruation starting day) is equal to or larger than a fourth predetermined number n4 (S24). The fourth predetermined number n4 determined in advance is, for example, five here. If the number of pieces of basal body temperature data within the scan range is less than the fourth predetermined number n4 (S24: NO), the estimation processing section 24 judges that estimation of an ovulation day is impossible (S25).

If the number of pieces of basal body temperature data within the scan range is equal to or larger than the fourth predetermined number n4 (S24: YES), the estimation processing section 24 detects a day when largest temperature increase occurs within the scan range from the scan starting day to a scan ending day decided at S24 (S26). The processes of S24 and S26 constitute a temperature increase detection section which detects temperature increase in basal body temperature increase, the largest temperature increase here, after the scan starting day within the scan range. That is, the processes of S24 and S26 constitute the temperature increase detection section which detects temperature increase in basal body temperature measured later relative to immediately previous basal body temperature measured earlier between chronologically adjacent pieces of basal body temperature data, among pieces of basal body temperature data between a menstruation starting day and a next menstruation starting day.

That is, the largest temperature increase indicating that temperature increase from immediately previous basal body temperature is the largest is detected within the scan range. More specifically, difference between temperatures of the scan starting day and a next day (that is, a value obtained by subtracting basal body temperature of the next day from basal body temperature of the scan starting day) is determined first. After that, a value of increase between two adjacent basal body temperatures within the scan range, that is, a value of increase of a day concerned relative to an immediately previous day is determined. The largest temperature increase is detected on the basis of multiple increase values determined.

After the largest temperature increase is detected, the estimation processing section 24 judges whether or not the largest temperature increase is larger than the fourth predetermined value d4 (S27). The fourth predetermined value d4 is, for example, 0.15° C. here. If the largest temperature increase is not larger than the fourth predetermined value d4 (S27: NO), the estimation processing section 24 judges that estimation of an ovulation day is impossible (S25). That is, when the temperature increase of the day when temperature increase is the largest compared to the immediately previous basal body temperature is equal to or lower than the fourth predetermined value d4, estimation impossibility, which means that estimation of an ovulation day is impossible, is judged.

If the largest temperature increase is larger than the fourth predetermined value d4 (S27: YES), the estimation processing section 24 sets a day when the largest temperature increase starts (that is, a day of basal body temperature data immediately before the day when the largest temperature increase occurs) as an estimated ovulation day candidate (S28). The day when the largest temperature increase occurs is a day when temperature increase compared to the chronologically immediately-previous basal body temperature is the largest. For example, if the largest temperature increase occurs between a day fourteen days before the menstruation starting day (a 15th day in FIG. 2) and a day thirteen days before the menstruation starting day (a 16th day in FIG. 2), the day thirteen days before the menstruation starting day (the 16th day in FIG. 2) is the day when temperature increase is the largest, and the day fourteen days before the menstruation starting day (the 15th day in FIG. 2) is the estimated ovulation day candidate.

Furthermore, if pieces of basal body temperature data of the day thirteen days before the menstruation starting day (the 16th day in FIG. 2) and the day fifteen days before the menstruation starting day (the 14th day in FIG. 2) exist, but basal body temperature data of the day fourteen days before the menstruation starting day (the 15th day in FIG. 2) does not exist, and the day thirteen days before the menstruation starting day (the 16th day in FIG. 2) is the day when temperature increase is the largest, then the day fifteen days before the menstruation starting day (the 14th day in FIG. 2) is the estimated ovulation day candidate.

After deciding the estimated ovulation day candidate, the estimation processing section 24 judges whether or not the estimated ovulation day, which is a candidate, is after the scan starting day, and difference between basal body temperature data of the estimated ovulation day and basal body temperature data immediately before the estimated ovulation day (that is, a value obtained by subtracting basal body temperature immediately before the estimated ovulation day from basal body temperature of the estimated ovulation day) is larger than a fifth predetermined value d5 (S29). The fifth predetermined value d5 is 0.1° C. here.

The process of S29 is a process for, when an estimated ovulation day candidate is once decided but difference between basal body temperature of the estimated ovulation day candidate day and basal body temperature of a day immediately before the estimated ovulation day candidate is equal to or larger than the predetermined value d5, changing the estimated ovulation day on the assumption that there was an ovulation day before the estimated ovulation day candidate.

If the estimated ovulation day is after the scan starting day, and the difference between the basal body temperature data of the estimated ovulation day and the basal body temperature data of the day immediately before the estimated ovulation day is larger than the fifth predetermined value d5 (S29: YES), the estimation processing section 24 sets the estimated ovulation day to the date of basal body temperature immediately before the estimated ovulation day candidate (S30). For example, even if the day fourteen days before the menstruation starting day (the 15th day in FIG. 2) once becomes the estimated ovulation day candidate, the day fifteen days before the menstruation starting day (the 14th day in FIG. 2) becomes the estimated ovulation day if the difference from the basal body temperature data of the day immediately before the estimated ovulation day candidate (the 14th day in FIG. 2) is larger than the fifth predetermined value d5.

As described above, the process from S28 to S30 constitutes an estimation section which estimates an ovulation day on the basis of the temperature increase detected at S26, that is, the largest temperature increase. Thus, in the process from S28 to S30, which is the estimation section, the ovulation day is estimated on the basis of a day when temperature increase is the largest, and a day of basal body temperature data immediately before the day when temperature increase compared to the immediately previous basal body temperature is the largest is estimated as the ovulation day. Furthermore, at S29 and S30, when the day when temperature increase is the largest, which is the estimated ovulation day, is after the scan starting day, and the difference between the basal body temperature immediately before the estimated ovulation day and the basal body temperature of the estimated ovulation day is larger than the fifth predetermined value (d5), the day of the basal body temperature data immediately before the estimated ovulation day (candidate day) is set as the ovulation day. That is, at S29 and S30, if temperature increase in the basal body temperature of the estimated ovulation day relative to the basal body temperature immediately before the estimated ovulation day is larger than the fifth predetermined value d5, the ovulation day is changed to the day of the basal body temperature data immediately before the estimated ovulation day.

In the case of NO at S29, the process ends.

When the ovulation day is estimated by S12, a previous day of the ovulation day is decided as the end of the low temperature period, and a day three days after the ovulation day is decided as the start of the high temperature period, with the estimated ovulation day as a base.

Note that, if the ovulation day cannot be estimated, the day sixteen days before the menstruation starting day is decided as the end of the low temperature period.

As described above, even if all pieces of basal body temperature data do not exist and some basal body temperature data is missing, estimation of an ovulation day is possible if the conditions described above are satisfied. Note that all the parameters such as each number of days, each coefficient, each predetermined value, each predetermined number, and specific numbers and values, which have been described with reference to each flowchart, are mere examples, and they are adjusted and set to appropriate values according to the users' basal body temperature data, apparatuses used or the like.

Returning to FIG. 3, after the ovulation day estimation process (S12) shown in FIG. 5 is executed, a type determination and score calculation process is executed (S13). The type determination and score calculation process is a process for determining a type of basal body temperature and calculating a score on the basis of the judged type.

The type determination is performed on the basis of change in basal body temperature data during the low temperature period and the high temperature period. Since an ovulation day is estimated by the ovulation day estimation process (S12) shown in FIG. 5, and the low temperature period and the high temperature period can be decided with the estimated ovulation day as a base, it is possible to accurately judge the user's state of hormone balance from a state of change in basal body temperature data.

That is, since influence of the hormone balance appears in basal body temperature, it is possible to, by determining a type of a basal body temperature graph, cause the judged type to be an indicator for knowing the state of hormone balance at a current time point.

Figure 6:
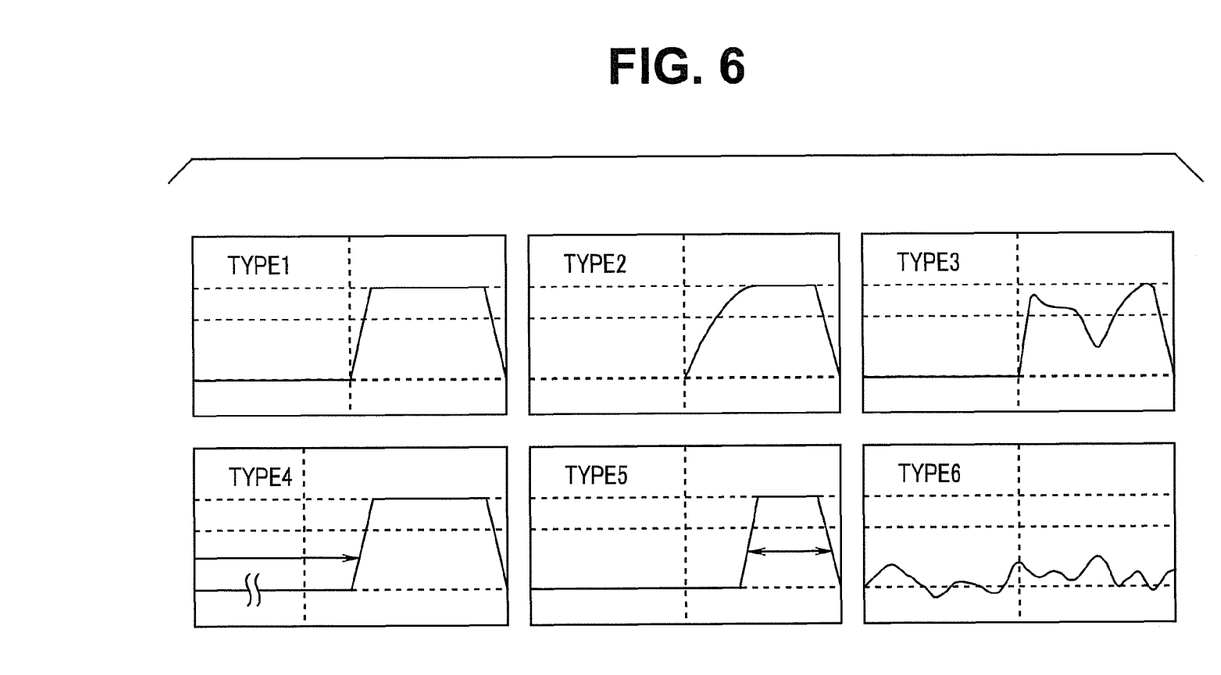
FIG. 6 is a diagram showing an example of types of basal body temperature according to the embodiment.

FIG. 6 is a diagram showing an example of types of basal body temperature. As shown in FIG. 6, change in basal body temperature differs among the types. The state of change in basal body temperature indicates the state of hormone balance.

A type 1 shows change in basal body temperature showing a normal hormone balance state. A type 2 shows change in basal body temperature in which body temperature gradually increases when transitioning from the low temperature period to the high temperature period. A type 3 shows change in basal body temperature in which there is a day when the body temperature lowers during the high temperature period. A type 4 shows change in basal body temperature in which the low temperature period is long, and the high temperature period is normal. A type 5 shows change in basal body temperature in which the high temperature period is short. A type 6 shows change in basal body temperature in which the period is not divided into two phases of the high temperature period and the low temperature period.

Note that such type classification of basal body temperature according to change in the basal body temperature may be performed in a classification method other than the type classification shown in FIG. 6.

After the type determination process (S13), a notification process is executed (S14). In the notification process, information about an estimated ovulation day and hormone balance state information are transmitted to the smartphone 2 of the user. Since the estimated ovulation day information transmitted from the server 4 is displayed on the smartphone 2, the user can refer to it to estimate the next ovulation day.

Figure 7:
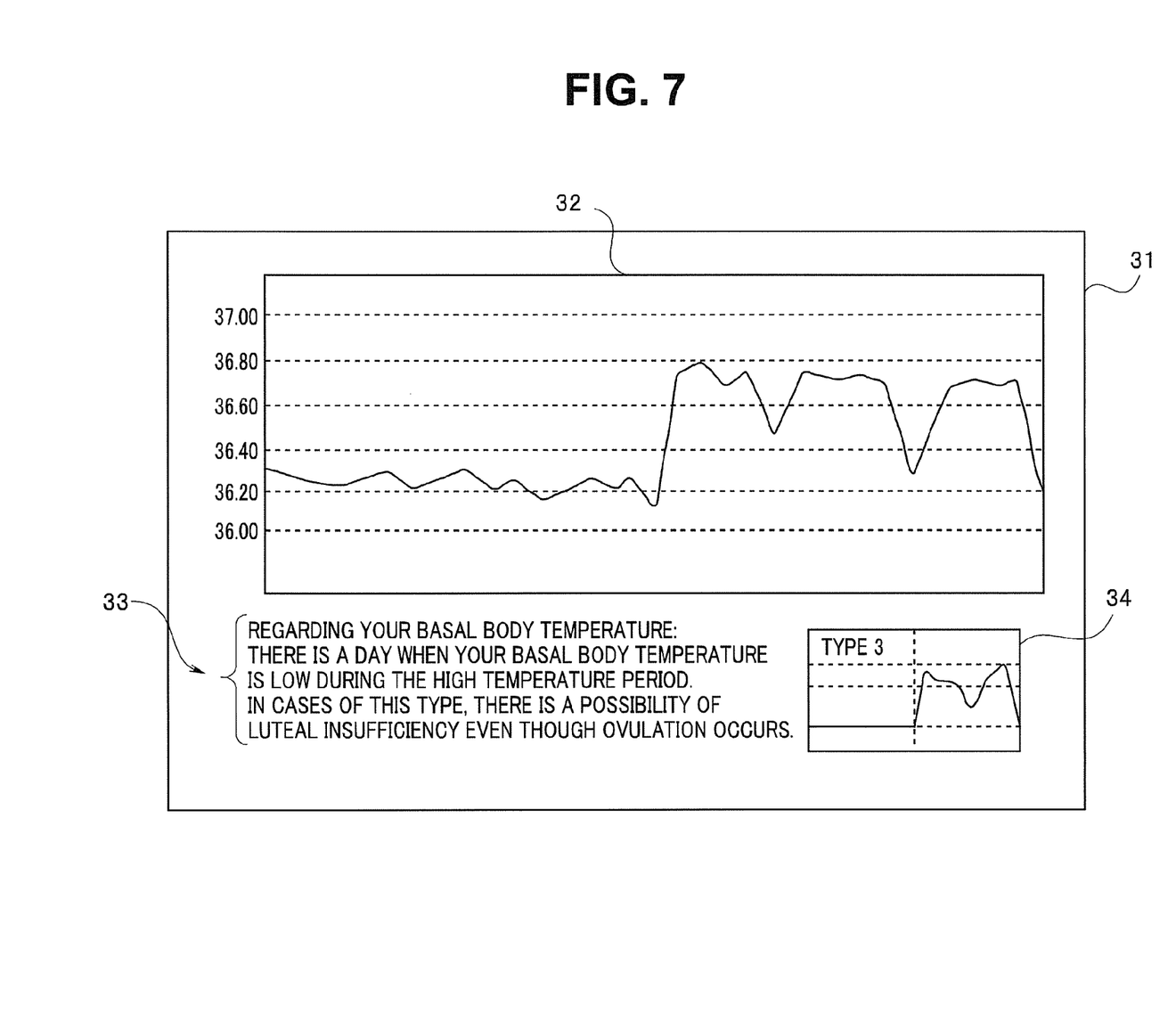
FIG. 7 is a diagram showing a screen example of hormone balance state information which a server 4 generates and transmits to a smartphone 2 according to the embodiment.

FIG. 7 is a diagram showing a screen example of the hormone balance state information which the server 4 generates and transmits to the smartphone 2. A screen as shown in FIG. 7 is displayed on the display section 14 of the smartphone 2.

A screen 31 has a graph display section 32 for displaying basal body temperature data of a latest menstrual cycle, a comment display section 33 for displaying a comment about the hormone balance state and a type display section 34 for showing a type of basal body temperature.

Thus, the user can know not only change in her basal body temperature data but also the hormone balance state information based on change in latest basal body temperature data.

Furthermore, the hormone balance state may be indicated by a score so that the user can easily understand it. That is, a quantified score may be calculated on the basis of a type and notified to the user.

Figure 8:
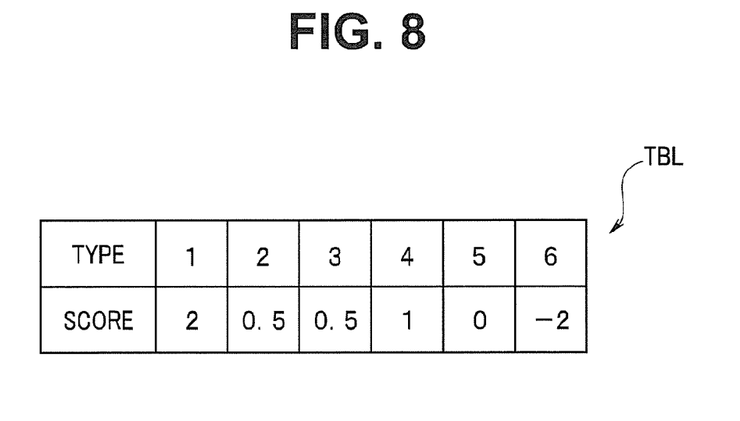
FIG. 8 is a diagram showing an example of table data TBL with which correspondences between types and scores are registered, according to the embodiment.

FIG. 8 is a diagram showing an example of table data TBL with which correspondences between types and scores are registered. In the table data TBL, 2, 0.5, 0.5, 1, 0 and −2 are allocated to types 1, 2, 3, 4, 5 and 6, respectively, as scores. The server 4 determines a score corresponding to a type judged for each menstrual cycle from the table data TBL and transmits the score to the smartphone 2.

Note that, instead of determining a score for each menstrual cycle, a total of scores of latest several cycles, for example, latest three menstrual cycles may be calculated and transmitted to the smartphone 2 by the server 4.

Thus, by calculating a score and presenting the score to the user, the user can quantitatively and intuitively know the hormone balance state.

As described above, the process of S13 constitutes a type determination section which judges a type of basal body temperature judged on the basis of change in the low temperature period and the high temperature period of basal body temperature data and a score calculation section which calculates a quantified score on the basis of the judged type.

The process of S14 constitutes a type information transmission section which transmits information about the judged type and a score information transmission section which transmits information about the calculated score.

Furthermore, at the time of notifying the user of, that is, showing the user an ovulation day estimation result and a basal body temperature analysis result, a statistical information result about other multiple users having the same attribute information as the user, for example, users regarded as belonging to a same group may be simultaneously notified to each group. For example, an average value of other users of a same generation may be displayed. As a result, the user can compare herself with others.

As described above, when each user inputs basal body temperature and a menstruation starting day to the smartphone 2 and transmits them to the server 4, the server 4 executes the processes from FIGS. 3 to 5 to estimate an ovulation day. Information about the estimated ovulation day is transmitted from the server 4 to the user's smartphone 2 via the network 3. Thus, the user accepts a notification of the estimated ovulation day information and can estimate the next ovulation day by referring to the notification.

As described above, according to the embodiment described above, it is possible to realize an ovulation day estimation apparatus capable of estimating an ovulation day, an ovulation day estimation method and an ovulation day estimation program.

Note that all or a part of a program for executing the operations described above is recorded or stored in a non-transitory computer-readable medium of a portable medium such as a flexible disk and a CD-ROM and a storage medium in which ovulation day estimation program is recorded such as a hard disk, as a computer program product. By the program being read by a computer, all or a part of the operations are executed. Otherwise, all or a part of the program can be distributed or provided via a communication network. By downloading the program via the communication network and installing the program into a computer or installing the program into the computer from a recording medium, a user can easily realize the ovulation day estimation apparatus of the present embodiment.

While certain embodiments have been described, these embodiments have been presented by way of example only, and are not intended to limit the scope of the inventions. Indeed, the novel methods and devices described herein may be embodied in a variety of other forms; furthermore, various omissions, substitutions and changes in the form of the methods and devices described herein may be made without departing from the spirit of the inventions. The accompanying claims and their equivalents are intended to cover such forms or modifications as would fall within the scope and spirit of the inventions.

What is claimed is:

1. An ovulation day estimation apparatus comprising a control section including a central processing unit, the control section causing the central processing unit to execute:
   a) calculating a first average basal body temperature in a high temperature period and a second average basal body temperature in a low temperature period from measured basal body temperature data, as chronological data, between a menstruation starting day and a next menstruation starting day;
b) provisionally setting a predetermined range between the menstruation starting day and the next menstruation starting day when a difference between the calculated first average basal body temperature and second average basal body temperature exceeds a first value;
c) deciding, as a starting day for detecting a largest temperature increase, an earliest day when detection of the largest temperature increase in which a difference between respective basal body temperature data within the predetermined range and basal body temperature data temporally immediately before the respective basal body temperature data is largest is performed in a chronological order, based on whether the respective basal body temperature data within the predetermined range satisfy a predetermined condition;
d) detecting a day on which the largest temperature increase occurred among the plurality of basal body temperature data from the decided starting day to an ending day which is a latest day within the predetermined range; and
e) estimating a day immediately before the day on which the largest temperature increase occurred as an ovulation day when the largest temperature increase is larger than a second value.

2. The ovulation day estimation apparatus according to claim 1, wherein the control section causes the central processing unit to judge estimation impossibility meaning that estimation of the ovulation day is not possible, when the largest temperature increase is equal to or smaller than the second value.

3. The ovulation day estimation apparatus according to claim 1, wherein the control section causes the central processing unit to decide, when several basal body temperature data that satisfy the predetermined condition exist, a latest day among the several basal body temperature data, as the scan starting day.

4. The ovulation day estimation apparatus according to claim 1, wherein the predetermined condition is that a value of a basal body temperature data within the predetermined range decreases from a value of a basal body temperature data immediately before the basal body temperature data by more than a third value and the value of the basal body temperature data is lower than a value obtained by adding a fourth value to the second average basal body temperature.

5. The ovulation day estimation apparatus according to claim 1,
wherein the control section causes the central processing unit to judge that a type of change in basal body temperature falls under which type of a plurality of types set in advance according to change in basal body temperature of the basal body temperature data; and
output information about the judged type.

6. The ovulation day estimation apparatus according to claim 5, wherein the control section causes the central processing unit to:
calculate a score quantified in advance according to the type, on the basis of the judged type; and
output information about the calculated score.

7. An ovulation day estimation method executed by a control section including a central processing unit, the central processing unit executing:
a) calculating a first average basal body temperature in a high temperature period and a second average basal body temperature in a low temperature period from measured basal body temperature data, as chronological data, between a menstruation starting day and a next menstruation starting day;
b) provisionally setting a predetermined range between the menstruation starting day and the next menstruation starting day when a difference between the calculated first average basal body temperature and second average basal body temperature exceeds a first value;
c) deciding, as a starting day for detecting a largest temperature increase, an earliest day when detection of the largest temperature increase in which a difference between respective basal body temperature data within the predetermined range and basal body temperature data temporally immediately before the respective basal body temperature data is largest is performed in a chronological order, based on whether the respective basal body temperature data within the predetermined range satisfy a predetermined condition;
d) detecting a day on which the largest temperature increase occurred among the plurality of basal body temperature data from the decided starting day to an ending day which is a latest day within the predetermined range; and
e) estimating a day immediately before the day on which the largest temperature increase occurred as an ovulation day when the largest temperature increase is larger than a second value.

8. The ovulation day estimation method according to claim 7, wherein the central processing unit judges estimation impossibility meaning that estimation of the ovulation day is not possible, when the largest temperature increase is equal to or smaller than the second value.

9. The ovulation day estimation method according to claim 7, wherein the central processing unit decides, when several basal body temperature data that satisfy the predetermined condition exist, a latest day among the several basal body temperature data, as the scan starting day.

10. The ovulation day estimation method according to claim 7, wherein the predetermined condition is that a value of a basal body temperature data within the predetermined range decreases from a value of a basal body temperature data immediately before the basal body temperature data by more than a third value and the value of the basal body temperature data is lower than a value obtained by adding a fourth value to the second average basal body temperature.

11. The ovulation day estimation method according to claim 7, wherein the central processing unit executes:
judging that a type of change in basal body temperature falls under which type of a plurality of types set in advance according to change in basal body temperature of the basal body temperature data; and
outputting information about the judged type.

12. A non-transitory storage medium in which ovulation day estimation program is recorded, the program causing a computer to execute:
a) a procedure for calculating a first average basal body temperature in a high temperature period and a second average basal body temperature in a low temperature period from measured basal body temperature data, as chronological data, between a menstruation starting day and a next menstruation starting day;
b) a procedure for provisionally setting a predetermined range between the menstruation starting day and the next menstruation starting day when a difference between the calculated first average basal body temperature and second average basal body temperature exceeds a first value;

c) a procedure for deciding, as a starting day for detecting a largest temperature increase, an earliest day when detection of the largest temperature increase in which a difference between respective basal body temperature data within the predetermined range and basal body temperature data temporally immediately before the respective basal body temperature data is largest is performed in a chronological order, based on whether the respective basal body temperature data within the predetermined range satisfy a predetermined condition;

d) a procedure for detecting a day on which the largest temperature increase occurred among the plurality of basal body temperature data from the decided starting day to an ending day which is a latest day within the predetermined range; and e) a procedure for estimating a day immediately before the day on which the largest temperature increase occurred as an ovulation day when the largest temperature increase is larger than a second value.

* * * * *